United States Patent
Goldstein et al.

(10) Patent No.: US 7,388,022 B2
(45) Date of Patent: Jun. 17, 2008

(54) POLYSUBSTITUTED 1,1-PYRIDYLAMINOCYCLOPROPANAMINE COMPOUNDS

(75) Inventors: Solo Goldstein, Suresnes (FR); Claude Guillonneau, Clamart (FR); Yves Charton, Sceaux (FR); Brian Lockhart, Feucherolles (FR); Pierre Lestage, La Celle Saint Cloud (FR)

(73) Assignee: Les Laboratoires Servier, Courbevoie Cedex (FR)

( * ) Notice: Subject to any disclaimer, the term of this patent is extended or adjusted under 35 U.S.C. 154(b) by 0 days.

(21) Appl. No.: 11/493,155

(22) Filed: Jul. 26, 2006

(65) Prior Publication Data

US 2007/0027192 A1 Feb. 1, 2007

(30) Foreign Application Priority Data

Jul. 28, 2005 (FR) .................................. 05 08032

(51) Int. Cl.
*C07D 213/74* (2006.01)
*A61K 31/44* (2006.01)
(52) U.S. Cl. ..................................... 514/352; 546/304
(58) Field of Classification Search ................. 546/304; 514/352

See application file for complete search history.

(56) References Cited

FOREIGN PATENT DOCUMENTS

| EP | 1170281 | 1/2002 |
|----|---------|--------|
| WO | 99/21834 | 5/1999 |
| WO | 0075110 | 12/2000 |
| WO | 0170733 | 9/2001 |
| WO | 0187288 | 11/2001 |

OTHER PUBLICATIONS

French Preliminary Search Report for FR05.08032 of Apr. 25, 2006.

*Primary Examiner*—Zinna N. Davis
(74) *Attorney, Agent, or Firm*—Hueschen and Sage

(57) ABSTRACT

A compound selected from those of formula (I):

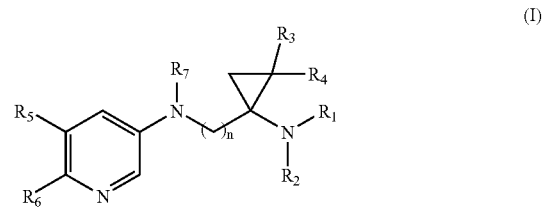

wherein:
n represents an integer from 1 to 6 inclusive,
$R_1$ and $R_2$ represent a hydrogen atom, a $(C_1-C_6)$alkyl group or an aryl-$(C_1-C_6)$alkyl group,
$R_3$ and $R_4$ represent a hydrogen atom or a $(C_1-C_6)$alkyl group,
$R_5$ and $R_6$ represent a hydrogen atom or a $(C_1-C_6)$alkyl, halogen, hydroxy, $(C_1-C_6)$alkoxy, cyano, nitro, $(C_2-C_6)$acyl, $(C_1-C_6)$alkoxycarbonyl, $(C_1-C_6)$trihaloalkyl or $(C_1-C_6)$-trihaloalkoxy group or an optionally substituted amino group,
$R_7$ represents a hydrogen atom, a $(C_1-C_6)$alkyl group or an arylalkyl group,
its enatiomers, diastereoisomers and additional salts thereof with a pharmaceutically acceptable acid or base.

Medicinal products containing the same which are useful in the treatment of conditions requiring a specific nicotinic ligand of α4β2 receptors.

8 Claims, No Drawings

POLYSUBSTITUTED 1,1-PYRIDYLAMINOCYCLOPROPANAMINE COMPOUNDS

The present invention relates to new polysubstituted 1,1-pyridylaminocyclopropanamine compounds, to a process for their preparation and to pharmaceutical compositions containing them.

The compounds of the present invention are especially valuable from a pharmacological point of view because of their specific interaction with central nicotinic receptors of type α4β2, having application in the treatment of neuropathologies associated with cerebral ageing, of mood disorders, of pain and of tobacco withdrawal.

Ageing of the population due to increased life expectancy at birth has brought with it a major increase in the incidence of age-related neuropathologies and especially of Alzheimer's disease. The principal clinical manifestations of cerebral ageing and especially of age-related neuropathologies are deficiencies in mnemic and cognitive functions, which may lead to dementia. It has been widely demonstrated that, of the various neuro-transmitters, acetylcholine plays a major role in memory functions and that there is large-scale destruction of the cholinergic neuronal pathways in certain neurodegenerative diseases or when there is inadequate activation in the case of cerebral ageing. For that reason, numerous therapeutic approaches have been aimed at preventing destruction of the neurotransmitter by means of the inhibition of acetylcholinesterase or have sought to provide a substitute for the deficient neurotransmitter. In the latter case, the cholinergic agonists proposed have been of the muscarinic type, which are specific for post-synaptic M1 receptors.

It has recently been shown that the cholinergic impairment associated with Alzheimer's disease affects neurones carrying nicotinic receptors more than those carrying muscarinic receptors (Schroder et al., "Alzheimer disease:therapeutic strategies", Birkhauser Boston, 1994, 181-185). Numerous studies have, moreover, demonstrated that nicotine has memory-facilitating properties (Prog. Neuropsychopharmacol., 1992, 16, 181-191) and that these properties are exerted as much on mnemic functions (Psychopharmacol., 1996, 123, 88-97) as on the faculties of attention and vigilance (Psychopharmacol., 1995, 118, 195-205). Furthermore, nicotine exerts neuroprotective effects with respect to excitotoxic agents such as glutamate (Brain Res., 1994, 644, 181-187).

All of these findings can very probably be linked with epidemiological studies that have shown a lower incidence of Alzheimer's disease and Parkinson's disease in smokers. Furthermore, several studies have shown the value of nicotine in the treatment of mood disorders such as states of depression, anxiety or schizophrenia. Finally, it has been shown that nicotine has antalgic properties. All of the therapeutic properties of nicotine and also those described for other nicotinic agents are based upon activity with respect to central receptors, which differ structurally and pharmacologically from peripheral receptors (muscle and ganglion). The central receptors of type α4β2 are the most represented in the central nervous system and have been implicated in the majority of the therapeutic effects of nicotine (Life Sci., 1995, 56, 545-570).

Several documents such as Synlett., 1999, 7, 1053-1054; J. Med. Chem, 1985, 28(12), 1953-1957 and 1980, 23(3), 339-341; 1970, 13(5), 820-826; 1972, 15(10), 1003-1006; J. Am. Chem. Soc., 1987, 109(13), 4036-4046, or a few patents or patent applications such as DE 36 08 727, EP 124 208 or WO 94/10158 describe and claim compounds containing a 1,1- or 1,2-disubstituted cyclopropane moiety. None of those references describe or suggest that those compounds have pharmacological activity that is specific for nicotinic receptors and, more especially, for central nicotinic receptors of type α4β2, this being a novel property of the compounds described by the Applicant. Patent Application EP 1 170 281 describes 1,1- and 1,2-disubstituted cyclopropane compounds which are nicotinic ligands.

The compounds of the present invention are therefore new and represent powerful selective nicotinic ligands of the central receptor sub-type α4β2. They are consequently of use in the treatment of deficiencies of memory associated with cerebral ageing and with neuro-degenerative diseases such as Alzheimer's disease, Parkinson's disease, Pick's disease, Korsakoff's disease and frontal lobe and subcortical dementias, and also for the treatment of mood disorders, Tourette's syndrome, attention-deficit hyperactivity syndrome, tobacco withdrawal and pain.

More specifically, the present invention relates to compounds of formula (I):

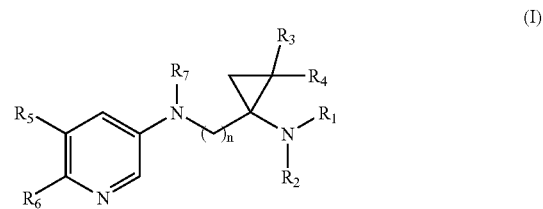

wherein:

n represents an integer of from 1 to 6 inclusive, $R_1$ and $R_2$, which may be identical or different, each independently of the other represent a hydrogen atom, a linear or branched ($C_1$-$C_6$)alkyl group or an aryl-($C_1$-$C_6$)alkyl group in which the alkyl moiety may be linear or branched, $R_3$ and $R_4$, which may be identical or different, each independently of the other represent a hydrogen atom or a linear or branched ($C_1$-$C_6$)alkyl group, $R_5$ and $R_6$ which may be identical or different, each independently of the other represent a hydrogen atom or a linear or branched ($C_1$-$C_6$)alkyl, halogen, hydroxy, linear or branched ($C_1$-$C_6$)alkoxy, cyano, nitro, linear or branched ($C_2$-$C_6$)acyl, linear or branched ($C_1$-$C_6$)alkoxycarbonyl, linear or branched ($C_1$-$C_6$)trihaloalkyl or linear or branched ($C_1$-$C_6$)trihaloalkoxy group or an amino group optionally substituted by one or two linear or branched ($C_1$-$C_6$)alkyl groups, $R_7$ represents a hydrogen atom, a linear or branched ($C_1$-$C_6$) alkyl group or an aryl-($C_1$-$C_6$)alkyl group in which the alkyl moiety may be linear or branched, there being understood by aryl group a phenyl, biphenyl, naphthyl, dihydronaphthyl, tetrahydronaphthyl, indanyl or indenyl group, each of those groups being optionally substituted by one or more identical or different groups selected from halogen atoms, linear or branched ($C_1$-$C_6$)alkyl, hydroxy, cyano, nitro, linear or branched ($C_1$-$C_6$)alkoxy, linear or branched ($C_2$-$C_7$)acyl, linear or branched ($C_1$-$C_6$) alkoxycarbonyl, linear or branched ($C_1$-$C_6$)trihaloalkyl and linear or branched ($C_1$-$C_6$)trihaloalkoxy groups and amino groups optionally substituted by one or two linear or branched ($C_1$-$C_6$)alkyl groups.

Preferred compounds of the invention are those compounds wherein n is an integer having the value 1.

The substituents $R_1$ and $R_2$ that are preferred according to the invention are a hydrogen atom and a linear or branched $(C_1$-$C_6)$alkyl group.

Even more preferably, the substituents $R_1$ and $R_2$ that are preferred according to the invention are a hydrogen atom and a methyl group.

The substituents $R_3$ and $R_4$ that are preferred according to the invention are a hydrogen atom.

The substituents $R_5$ and $R_6$ that are preferred according to the invention are a hydrogen atom, a linear or branched $(C_1$-$C_6)$alkyl group and a halogen atom.

Advantageously, preferred compounds of the invention are the compounds wherein $R_5$ represents a hydrogen atom and $R_6$ represents a linear or branched $(C_1$-$C_6)$alkyl group or a halogen atom.

Even more advantageously, preferred compounds of the invention are the compounds wherein $R_5$ represents a hydrogen atom and $R_6$ represents a methyl group or a halogen atom.

The substituent $R_7$ preferred according to the invention is a hydrogen atom or a linear or branched $(C_1$-$C_6)$alkyl group.

Advantageously, the substituent $R_7$ preferred according to the invention is a hydrogen atom or a methyl group.

In especially advantageous manner, preferred compounds of the invention are:

N-{[1-(methylamino)cyclopropyl]methyl}pyridin-3-amine
N-methyl-N-{[1-(methylamino)cyclopropyl]methyl}pyridin-3-amine
N-[(1-aminocyclopropyl)methyl]pyridin-3-amine
N-{[1-(dimethylamino)cyclopropyl]methyl}pyridin-3-amine
N-[(1-aminocyclopropyl)methyl]-N-methylpyridin-3-amine
N-{[1-(dimethylamino)cyclopropyl]methyl}-N-methylpyridin-3-amine
6-chloro-N-{[1-(methylamino)cyclopropyl]methyl}pyridin-3-amine
6-chloro-N-methyl-N-{[1-(methylamino)cyclopropyl]methyl}pyridin-3-amine
6-bromo-N-{[1-(methylamino)cyclopropyl]methyl}pyridin-3-amine
6-bromo-N-methyl-N-{[1-(methylamino)cyclopropyl]methyl}pyridin-3-amine
6-methyl-N-{[1-(methylamino)cyclopropyl]methyl}pyridin-3-amine
N,6-dimethyl-N-{[1-(methylamino)cyclopropyl]methyl}pyridin-3-amine Among the pharmaceutically acceptable acids there may be mentioned, without implying any limitation, hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, camphoric acid etc.

Among the pharmaceutically acceptable bases there may be mentioned, without implying any limitation, sodium hydroxide, potassium hydroxide, triethylamine, tert-butylamine etc.

The enantiomers, diastereoisomers, and also addition salts thereof with a pharmaceutically acceptable acid or base of the preferred compounds form an integral part of the invention.

The present invention relates also to a process for the preparation of compounds of formula (I), which is characterised in that there is used as starting material a compound of formula (II):

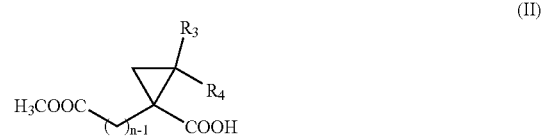

wherein $R_3$, $R_4$ and n are as defined for formula (I), which compounds of formula (II) are reacted with diphenylphosphoryl azide in the presence of triethyleneamine in toluene, followed by the addition of tert-butanol, to yield compounds of formula (III):

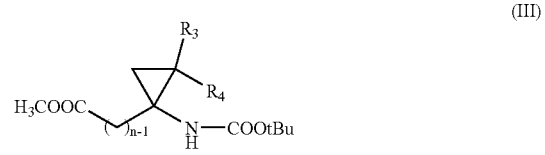

wherein $R_3$, $R_4$ and n are as defined above, which compounds of formula (III) are reacted with a compound of formula (IV):

wherein Hal represents a halogen atom and $R'_1$ represents a group selected from linear or branched $(C_1$-$C_6)$alkyl and aryl-$(C_1$-$C_6)$alkyl in which the alkyl moiety may be linear or branched, in the presence of a base in an anhydrous solvent, to yield compounds of formula (V):

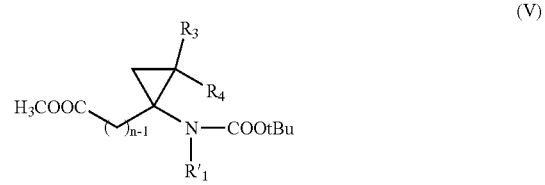

wherein $R_3$, $R_4$, n and $R'_1$ are as defined above, the compounds of formulae (III) and (V) constituting the compounds of formula (VI):

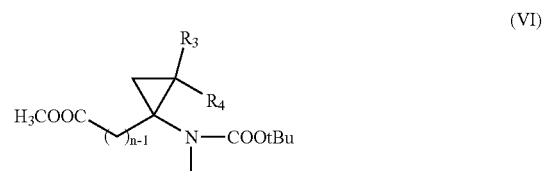

wherein $R_3$, $R_4$ and n are as defined above and $R_1$ is as defined for formula (I), which compounds of formula (VI) are placed in the presence of a reducing agent to yield compounds of formula (VII):

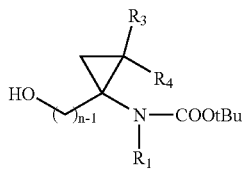
(VII)

wherein $R_3$, $R_4$, n and $R_1$ are as defined above,
which compounds of formula (VII) are subjected to the action of an oxidising agent conventional in organic synthesis to yield compounds of formula (VIII):

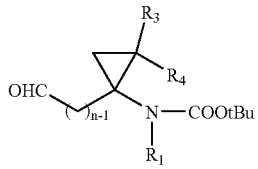
(VIII)

wherein $R_3$, $R_4$, n and $R_1$ are as defined above,
which compounds of formula (VIII) are reacted with a compound of formula (IX):

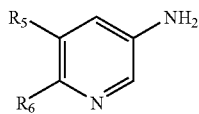
(IX)

wherein $R_5$ and $R_6$ are as defined for formula (I), in the presence of sodium triacetoxyborohydride, to yield compounds of formula (X):

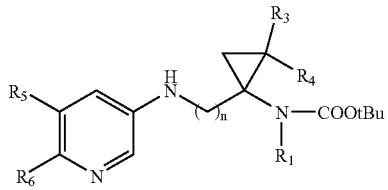
(X)

wherein $R_3$, $R_4$, $R_5$, $R_6$, n and $R_1$ are as defined above,
which compounds of formula (X) are:
either placed in the presence of an acid in dioxane to yield compounds of formula (I/a), a particular case of the compounds of formula (I):

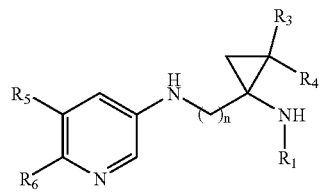
(I/a)

wherein $R_1$, $R_3$, $R_4$, $R_5$, $R_6$ and n are as defined above,
which compounds of formula (I/a) are:
either placed in the presence of an aqueous solution of formaldehyde and formic acid to yield compounds of formula (I/b), a particular case of the compounds of formula (I):

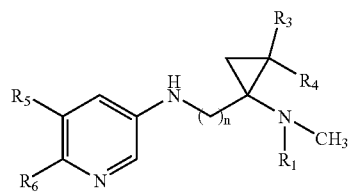
(I/b)

wherein $R_1$, $R_3$, $R_4$, $R_5$, $R_6$ and n are as defined above,
either reacted with a compound of formula (XI):

R'$_2$-Hal (XI)

wherein Hal is as defined above and R'$_2$ represents a group selected from linear or branched $(C_1$-$C_6)$alkyl and aryl-$(C_1$-$C_6)$alkyl in which the alkyl moiety may be linear or branched, in the presence of a base in an anhydrous solvent, to yield compounds of formula (I/c), a particular case of the compounds of formula (I):

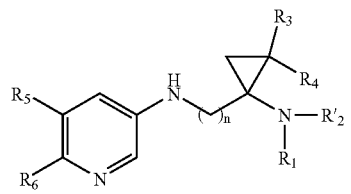
(I/c)

wherein $R_1$, $R_3$, $R_4$, $R_5$, $R_6$, n and R'$_2$ are as defined above,
either, when $R_1$ represents a benzyl group, placed in the presence of hydrochloric acid and palladium-on-carbon to yield compounds of formula (I/d), a particular case of the compounds of formula (I):

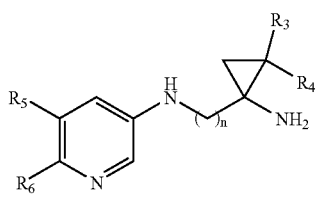

(I/d)

wherein $R_3$, $R_4$, $R_5$, $R_6$ and n are as defined above, which compounds of formula (I/d) are treated with formic acid and an aqueous formaldehyde solution to yield compounds of formula (I/e), a particular case of the compounds of formula (I):

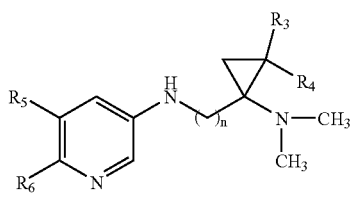

(I/e)

wherein $R_3$, $R_4$, $R_5$, $R_6$ and n are as defined above, the compounds of formulae (I/b), (I/c), (I/d) and (I/e) constituting the compounds of formula (I/f), a particular case of the compounds of formula (I):

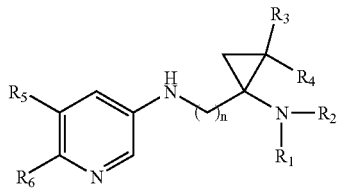

(I/f)

wherein $R_1$, $R_2$, $R_3$, $R_4$, $R_5$, $R_6$ and n are as defined above, which compounds of formula (I/f) are reacted with a compound of formula (XII):

R'$_7$—COOH    (XII), wherein R'$_7$ represents a group selected from linear or branched ($C_1$-$C_5$)alkyl and aryl-($C_1$-$C_5$)alkyl in which the alkyl moiety may be linear or branched, in the presence of a coupling agent, followed by reduction of the amide, to yield compounds of formula (I/g), a particular case of the compounds of formula (I):

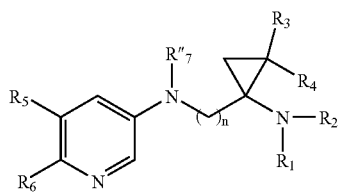

(I/g)

wherein $R_1$, $R_2$, $R_3$, $R_4$, $R_5$, $R_6$ and n are as defined above and R"$_7$ represents a group selected from linear or branched ($C_1$-$C_6$)alkyl and aryl-($C_1$-$C_6$)alkyl in which the alkyl moiety may be linear or branched, either placed in the presence of carbonyldiimidazole and formic acid in dimethylformamide to yield compounds of formula (XIII):

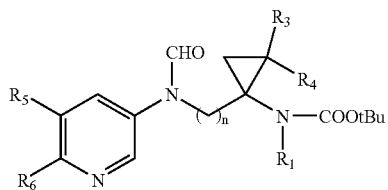

(XIII)

wherein $R_1$, $R_3$, $R_4$, $R_5$, $R_6$ and n are as defined above, which compounds of formula (XIII) are reacted with borane-methyl sulphide complex in tetrahydrofuran to yield compounds of formula (XIV):

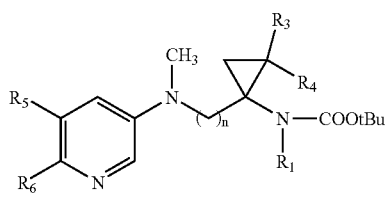

(XIV)

wherein $R_1$, $R_3$, $R_4$, $R_5$, $R_6$ and n are as defined above, which compounds of formula (XIV) are subjected to the same reaction conditions as the compounds of formula (X), the action of acid in dioxane, to yield compounds of formula (I/h), a particular case of the compounds of formula (I):

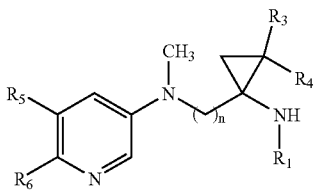

(I/h)

wherein $R_1$, $R_3$, $R_4$, $R_5$, $R_6$ and n are as defined above, which compounds of formula (I/h), when $R_1$ represents a benzyl group, are subjected to the same reaction conditions as the compounds of formula (I/a) to yield compounds of formula (I/i), particular cases of the compounds of formula (I):

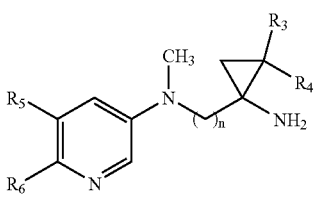

(I/i)

wherein $R_3$, $R_4$, $R_5$, $R_6$ and n are as defined above, which compounds of formula (I/i) are subjected to the same reaction conditions as the compounds of formula (I/d) to yield compounds of formula (I/j), particular cases of the compounds of formula (I):

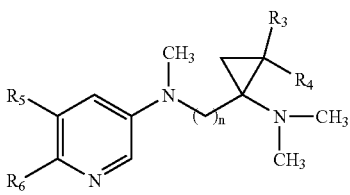

(I/j)

wherein $R_3$, $R_4$, $R_5$, $R_6$ and n are as defined above, the totality of the compounds of formulae (I/a) to (I/j) constituting the totality of the compounds of the invention, which are purified, where appropriate, according to conventional purification techniques, which may be separated into their different isomers according to a conventional separation technique, and which are converted, where appropriate, into addition salts thereof with a pharmaceutically acceptable acid or base.

The compounds of formulae (II), (IV), (IX), (XI) and (XII) are either commercial products or are obtained according to conventional methods of organic synthesis well known to the person skilled in the art.

Generally, isomers of the compounds of the invention are understood to be optical isomers such as enantiomers and diastereoisomers. More especially, pure enantiomeric forms of the compounds of the invention may be separated by starting from mixtures of enantiomers which are reacted with a racemate-separating agent that can be released, the said agent being itself in the form a pure enantiomer, which allows the corresponding diastereoisomers to be obtained. The diastereoisomers are then separated according to separation techniques well known to the person skilled in the art, such as crystallisation or chromatography, and the separating agent is then removed using conventional techniques of organic chemistry, resulting in a pure enantiomer being obtained.

The compounds of the invention that are present in the form of a mixture of diastereoisomers are isolated in a pure form by using conventional separation techniques such as chromatography.

In certain particular cases, the process for the preparation of compounds of the invention may result in the predominant formation of one enantiomer or diastereoisomer over the other.

By virtue of their pharmacological properties as nicotinic ligands, and their selectivity for the receptor sub-type α4β2, the compounds of the present invention are of use in the treatment of deficiencies of memory associated with cerebral ageing and neurodegenerative diseases such as Alzheimer's disease, Parkinson's disease, Pick's disease, Korsakoff's disease and frontal lobe and subcortical dementias, and also for the treatment of mood disorders, Tourette's syndrome, attention-deficit hyperactivity syndrome, tobacco withdrawal and pain.

The present invention relates also to pharmaceutical compositions comprising as active ingredient at least one compound of formula (I), an isomer thereof, or an addition salt thereof with a pharmaceutically acceptable acid or base, alone or in combination with one or more pharmaceutically acceptable, inert, non-toxic excipients or carriers.

Pharmaceutical compositions according to the invention for parenteral injections include, especially, aqueous and non-aqueous sterile solutions, dispersions, suspensions and emulsions, and also sterile powders for reconstituting injectable solutions or dispersions.

Pharmaceutical compositions according to the invention for oral administration in solid form include, especially, tablets or dragées, sublingual tablets, sachets, gelatin capsules and granules and, for oral, nasal, buccal or ocular administration in liquid form, include, especially, emulsions, solutions, suspensions, drops, syrups and aerosols.

Pharmaceutical compositions for rectal or vaginal administration are preferably suppositories, and those for per- or trans-cutaneous administration include, especially, powders, aerosols, creams, ointments, gels and patches.

The pharmaceutical compositions mentioned hereinbefore illustrate the invention but do not limit it in any way.

Among the pharmaceutically acceptable, inert, non-toxic excipients or carriers there may be mentioned, by way of non-limiting example, diluents, solvents, preservatives, wetting agents, emulsifiers, dispersing agents, binders, swelling agents, disintegrating agents, retardants, lubricants, absorbents, suspending agents, colorants, flavourings etc.

The useful dosage varies according to the age and weight of the patient, the administration route and the pharmaceutical composition used, the nature and severity of the disorder and the administration of any associated treatments. The dosage ranges from 1 mg to 500 mg per day in one or more administrations.

The Examples that follow illustrate the invention but do not limit it in any way.

The starting materials used are products that are known or that are prepared according to known operating procedures. The various Preparations yield synthesis intermediates that are useful in the preparation of the compounds of the invention.

The structures of the compounds described in the Examples and Preparations were determined according to the usual spectrophotometric techniques (infrared, nuclear magnetic resonance, mass spectrometry, . . . ).

The melting points were determined using either a Kofler hot-plate or a hot-plate under a microscope. When the compound is in the form of a salt, the melting point given and the elemental microanalysis refer to the salt form of the product.

PREPARATION I: tert-Butyl 1-(formyl)cyclopropyl(methyl)carbamate

Step 1: Methyl 1-[(tert-butoxycarbonyl)amino]cyclopropanecarboxylate

A solution of 80 g of 1-(methoxycarbonyl)cyclopropanecarboxylic acid and 78 ml of triethylamine in 550 ml of toluene, to which 152 g of diphenylphosphoryl azide is added, is heated to 80° C. When the evolution of gas has ceased, the temperature is brought to 50° C. and 61 g of tert-butanol are added. After 7 hours' reaction at 80° C., the mixture is concentrated. The residue is taken up in ether, washed with saturated $Na_2CO_3$ solution, then with 1N hydrochloric acid solution, and then with $NaHCO_3$ solution. After drying and evaporation of the organic phase, the residue is taken up in 300 ml of cyclohexane and then concentrated to dryness. The residue obtained is triturated in pentane, filtered and then dried, allowing the expected product to be isolated.

Step 2: Methyl 1-[(tert-butoxycarbonyl)(methyl)amino]cyclopropanecarboxylate 24.7 g of sodium hydride are added in portions to a solution, cooled to 5° C., of 99.7 g of the compound obtained in the above Step 1 in 1.7 l of anhydrous dimethylformamide. After 15 minutes at 5° C. and then 3 hours at ambient temperature, 38.2 ml of methyl iodide are added dropwise. After reaction for 20 hours, the mixture is evaporated. The residue is taken up in ether and then treated in conventional manner. Chromatography on silica gel (dichloromethane) allows the expected product to be isolated.

Step 3: tert-Butyl 1-(hydroxymethyl)cyclopropyl(methyl)carbamate

A solution of 100 ml of 2M lithium borohydride in tetrahydrofuran is added to a solution of 23 g of the compound obtained in the above Step 2 in 100 ml of tetrahydrofuran. After stirring for 20 hours at ambient temperature, then 8 hours at reflux, the reaction mixture is cooled to 0° C., hydrolysed, diluted with ether, separated, dried and concentrated. Chromatography of the residue on silica gel (dichloromethane/tetrahydrofuran: 95/5) allows the expected product to be isolated.

Step 4: tert-Butyl 1-formylcyclopropyl(methyl)carbamate 33.5 g of dimethyl sulphoxide are added at –60° C., over a period of 20 minutes, to a solution containing 25.8 g of oxalyl chloride in 430 ml of dichloromethane. After stirring for 20 minutes at –60° C., a mixture containing 34.3 g of the compound of the above Step 3 in 100 ml of dichloromethane is added at –60° C. over a period of 1 hour. After stirring for 30 minutes at –60° C., 81 ml of triethylamine is poured in over a period of 20 minutes at –60° C. and then the temperature is allowed to rise to 20° C. again. 60 ml of water are poured in, separation is carried out and the aqueous phase is extracted several times with dichloromethane. The combined dichloromethane phases are washed with saturated sodium chloride solution and dried over sodium sulphate and then concentrated to dryness. Chromatography on silica gel (dichloromethane/tetrahydrofuran: 97/3) allows 31.2 g of the expected product to be obtained.

PREPARATION 2: tert-Butyl benzyl{1-[(pyridin-3-ylamino)methyl]cyclopropyl}-carbamate Step 1: Methyl 1-[benzyl(tert-butoxycarbonyl)amino]cyclopropanecarboxylate 21.5 g of the compound of Step 1 of Preparation 1 and 216 ml of dimethylformamide are introduced into a three-necked flask. At 20° C., 4.8 g of 60% sodium hydride in oil are added. Stirring is carried out for 2 hours at ambient temperature. Over a period of 20 minutes, 18 ml of benzyl bromide are poured in and stirring is carried out for 20 hours at ambient temperature. Heating is carried out for 1 hour at 60° C. followed by concentration to dryness. The residue is taken up in ether, and washed with 10% sodium carbonate solution and then with 10% lithium chloride solution. Drying over sodium sulphate and concentration to dryness are carried out. Chromatography on silica gel (dichloromethane/cyclohexane: 85/15 then pure dichloromethane) allows 21.3 g of the expected product to be obtained in the form of a gum.

Step 2: tert-Butyl benzyl[1-(hydroxymethyl)cyclopropyl]carbamate

Over a period of 20 minutes, 70 ml of 2M lithium borohydride in THF are poured at 20° C. into a mixture of 21.2 g of the compound obtained in the above Step 1 and 100 ml of tetrahydrofuran. Stirring is carried out for 20 hours at 20° C. and then for 1 hour at reflux. Cooling to 5° C. is carried out followed by cautious hydrolysis with 24 ml of water and then with 20 ml of 10% aqueous sodium carbonate solution. 500 ml of ether are added, separation is carried out and the aqueous phase is extracted with ether. The combined ethereal phases are dried over sodium sulphate and concentrated to dryness. 19.3 g of the expected product are obtained.

Melting point: 68° C.

Step 3: tert-Butyl benzyl(1-formylcyclopropyl)carbamate

Over a period of 20 minutes, 10.3 ml of dimethyl sulphoxide are poured at –60° C. into a mixture of 7.94 ml of oxalyl chloride and 145 ml of dichloromethane. The mixture is stirred for 20 minutes at –60° C. 19.3 g of the compound obtained in the above Step 2 are poured in over a period of 1 hour and stirring is carried out for 30 minutes at –60° C. 27.3 ml of triethylamine are poured in and stirring is carried out for 20 minutes at –60° C. The temperature is allowed to rise to 20° C. and 50.6 ml of water are poured in. After stirring for 10 minutes at 20° C., separation is carried out and the aqueous phase is extracted with dichloromethane. The combined organic phases are dried over sodium sulphate and concentrated to dryness. Chromatography on silica gel (dichloromethane) allows 16.45 g of the expected product to be obtained.

Melting point: 67° C.

Step 4: tert-Butyl benzyl{1-[(pyridin-3-ylamino)methyl]cyclopropyl}carbamate 38.8 g of the product obtained in the above Step 3, 14.7 g of 3-aminopyridine and 282 ml of 3 Å molecular sieve are added to 2.5 l of dichloromethane. Stirring is carried out for 2 hours at 20° C. and then 149 g of sodium triacetoxyborohydride are added. Stirring is carried out for 4 days at 20° C. Filtration is carried out and the filtrate is washed with 10% aqueous sodium carbonate solution, dried over sodium sulphate and concentrated to dryness. Chromatography on silica gel (dichloromethane/tetrahydrofuran: 90/10) allows 36.2 g of the expected product to be obtained in the form of a gum.

EXAMPLE 1

N-{[1-(Methylamino)cyclopropyl]methyl}pyridin-3-amine dihydrochloride

Step 1: tert-Butyl methyl{1-[(pyridin-3-ylamino)methyl]cyclopropyl}carbamate 15.9 g of sodium triacetoxyborohydride are added at 20° C., under a nitrogen atmosphere, to a mixture containing 3.0 g of product of Preparation 1, 300 ml of dichloromethane, 1.56 g of 3-aminopyridine and 30 ml of 3 Å molecular sieve. The reaction mixture is stirred for 2 days at 20° C. and filtered. The filtrate is washed with 10% sodium carbonate solution, dried over sodium sulphate and concentrated to dryness. Chromatography on silica gel (toluene/ethanol: 95/5) allows 3.0 g of the expected product to be obtained.

Step 2: N-{[1-(Methylamino)cyclopropyl]methyl}pyridin-3-amine dihydrochloride At 20° C., 14 ml of 4N hydrochloric acid in dioxane are poured into a solution containing 1.0 g of the product obtained in the above Step 1 in 50 ml of dioxane. Stirring is carried out for 20 hours at ambient temperature. Ether is added, and insoluble material is suction-filtered off and dissolved in ethanol. Concentration to dryness is carried out and the residue is triturated in ether. The crystals are suction-filtered off and dried in vacuo at 30° C. 0.78 g of expected product are obtained.

Mass spectrometry (ESI): m/z=178.1 Th ([M+H]$^+$)
Melting point: 190-195° C.

EXAMPLE 2

N-Methyl-N-{[1-(methylamino)cyclopropyl]methyl}pyridin-3-amine dihydrochloride

Step 1: tert-Butyl (1-{[formyl(pyridin-3-yl)amino]methyl}cyclopropyl(methyl)-carbamate A solution of 23.8 g of carbonyldiimidazole and 30 ml of DMF is poured at 5° C. into a solution containing 6.14 g of formic acid and 30 ml of DMF. Stirring is carried out for 1 hour at 5° C. and then for 3 hours at 20° C. Cooling to 5° C. is carried out and then a mixture containing 7.4 g of product obtained in Step 1, Example 1 and 75 ml of DMF is poured in. Stirring for 20 hours at 20° C. and concentration to dryness under 1 torr are carried out. The residue is taken up in dichloromethane, washed with 10% aqueous sodium carbonate solution, dried over sodium sulphate and then concentrated to dryness. Chromatography on silica gel (toluene/ethanol: 95/5) allows 6.2 g of expected product to be obtained.

Step 2: N-Methyl-N-{[1-(methylamino)cyclopropyl]methyl}pyridin-3-amine dihydrochloride At 0° C., 1.6 ml of 10M borane-methyl sulphide complex is poured into a mixture containing 2.0 g of compound obtained in the above Step 1 and 20 ml of tetrahydrofuran. The temperature is allowed to rise to 40° C. and then refluxing is carried out for 3 hours. Cooling to 0° C. is carried out and then 3 ml of methanol are poured in. Stirring is carried out for 1 hour and then hydrochloric methanol is slowly poured in until a pH<2 is reached. Evolution of gas is observed. When the evolution ceases, refluxing is carried out for 3 hours. Concentration to dryness is carried out. The residue is taken up in dichloromethane and then washed with 1N sodium hydroxide solution. Drying over sodium sulphate and concentration to dryness are carried out. The residue is chromatographed on silica gel (dichloromethane/methanol/ammonium hydroxide 15N: 95/5/0.5). 0.7 g of base is obtained which is dissolved in ether. Ethereal hydrogen chloride is added until an acid pH is reached. Precipitation is observed. The ether is separated off and the gum is triturated with pure ether. Crystallisation is observed. The crystals are suction-filtered off and dried at 40° C. under 1 torr. 0.8 g of expected product is obtained.

Mass spectrometry (ESI): m/z=192.1 Th ([M+H]$^+$)
Melting point: 180-184° C.

EXAMPLE 3

N-{[1-Benzylamino)cyclopropyl]methyl}pyridin-3-amine 50 ml of 4M hydrochloric acid in dioxane are added at 20° C. to a mixture containing 7.15 g of the compound of Preparation 2, 80 ml of dioxane and 80 ml of methanol. Stirring is carried out for 3 days at 20° C. Concentration to dryness is carried out, methanol is added, concentration is carried out again, and the addition and distilling off of methanol are repeated a further twice. The residue is taken up in 300 ml of methanol and 80 ml of silica gel are added. Concentration to dryness is carried out (paste formation). Chromatography on silica gel (CH$_2$Cl$_2$/methanol: 80/20) allows 6.6 g of expected product in the form of a gum to be obtained.

EXAMPLE 4

N-[(1-Aminocyclopropyl)methyl]pyridin-3-amine dihydrochloride 4.0 g of the compound of Example 3 are dissolved in 200 ml of ethanol and 1.0 ml of 11.8N hydrochloric acid are added. Concentration to dryness is carried out and the residue is dissolved in 200 ml of ethanol with reflux. After cooling, 200 ml of cyclohexene are added and then, under a nitrogen atmosphere, 1.2 g of 10% palladium-on-carbon. Refluxing is carried out for 20 hours, followed by filtration and concentration to dryness. The residue is taken up in 200 ml of ethanol and 5 ml of water and concentrated again. The residue is dissolved in methanol and 32 ml of silica gel are added (paste formation). Concentration to dryness is carried out. Chromatography on 550 ml of silica gel (dichloro-methane/methanol: 80/20) is carried out. A compound is obtained which is taken up in 12 ml of 35% sodium hydroxide solution. Extraction is carried out several times with ether, and the combined ethereal phases are dried over sodium sulphate and concentrated to dryness. The residue is dissolved in ethanol, hydrochloric ethanol is added until pH 1 is reached and concentration to dryness is carried out. The residue is dissolved in isopropanol with heating, and cooled, which causes crystallisation. The crystals are suction-filtered off and dried at 50° C. under 0.5 torr. 1.6 g of expected product is obtained.

Mass spectrometry (EI): m/z=163.1 Th (M⁺)
Melting point: 195-199° C.

EXAMPLE 5

N-{[1-(Dimethylamino)cyclopropyl]methyl}pyridin-3-amine dihydrochloride 1.26 g of base of the compound of Example 4 are dissolved in 25.2 ml of formic acid and 25.2 ml of 37% formaldehyde. Heating is carried out for 5 hours at 70° C. Concentration to dryness is carried out and the residue is taken up in 20 ml of water and concentrated again. The residue is taken up in 15 ml of 35% sodium hydroxide solution and extracted with ether, and the combined ethereal phases are dried over sodium sulphate and concentrated to dryness. The residue is chromatographed on 230 ml of silica gel (dichloromethane/methanol: 95/5) and 1.17 g of residue is obtained which is dissolved in 25 ml of isopropanol. 3 ml of 4M hydrochloric acid in dioxane are added and then dilution with 25 ml of ether is carried out. The crystals are suction-filtered off and dried and 1.25 g of expected product is obtained.

Mass spectrometry (ESI): m/z=192.1 Th ([M+H]⁺)
Melting point: 208-210° C.

EXAMPLE 6

N-{[1-(Benzylamino)cyclopropyl]methyl}-N-methylpyridin-3-amine

Step 1: tert-Butyl benzyl(1-{(formyl(pyridin-3-yl)amino]methyl}cyclopropyl)carbamate The compound is obtained according to the procedure of Step 1 of Example 2, with replacement of the compound of Step 1 of Example 1 with the compound of Preparation 2.

Step 2: N-{[1-(benzylamino)cyclopropyl]methyl}-N-methylpyridin-3-amine

The compound is obtained according to the procedure of Step 2 of Example 2, using the compound of the above Step 1.

EXAMPLE 7

N-{(1-Aminocyclopropyl)methyl]-N-methylpyridin-3-amine dihydrochloride 5.5 ml of 11.8N hydrochloric acid are added to a mixture containing 17.7 g of the compound of Example 6 and 900 ml of ethanol. The mixture is made tepid to obtain a solution. 900 ml of cyclohexene are added and then, under a nitrogen atmosphere, 6 g of 10% palladium-on-carbon. Refluxing is carried out for 20 hours. The catalyst is filtered off and the filtrate is concentrated to dryness. The residue is taken up in 60 ml of 35% sodium hydroxide solution and extraction is carried out with a copious amount of ether. The combined ethereal phases are dried over sodium sulphate and concentrated to dryness. The residue is chromatographed on silica gel (dichloromethane/methanol: 93/7). The base of the desired product is obtained, which is converted to a salt by addition of hydrochloric acid in slight excess in ethanol. Dilution is carried out with ether. The crystals are suction-filtered off and dried at 40° C. under 1 torr. 2.48 g of expected product are obtained.

Mass spectrometry (ESI): m/z=178.1 Th ([M+H]⁺)
Melting point: 218-222° C.

EXAMPLE 8

N-{[1-(Dimethylamino)cyclopropyl]methyl}-N-methylpyridin-3-amine dihydrochloride The compound is obtained according to the procedure of Example 5, with replacement of the compound of Example 4 with the compound of Example 7.

Mass spectrometry (ESI): m/z=206.2 Th ([M+H]⁺)
Melting point: 198-201° C.

EXAMPLE 9

6-Chloro-N-{[1-(methylaminocyclopropyl)methyl}pyridin-3-amine dihydrochloride

Step 1: tert-Butyl (1-{[(6-chloropyridin-3-yl)amino]methyl}cyclopropyl)-methylcarbamate 10 ml of acetic acid are added to a mixture containing 10.8 g of the compound of Preparation 1, 100 ml of methanol and 6.9 g of 5-amino-2-chloropyridine. Stirring is carried out for 30 minutes at ambient temperature. Cooling to 5° C. is carried out and 4.4 g of sodium cyanoborohydride are added in portions. Stirring is carried out for 20 hours at 20° C. 10 ml of water are added and concentration to dryness is carried out. The residue is taken up in dichloromethane and aqueous potassium carbonate solution. Separation is carried out and the aqueous phase is extracted several times with dichloromethane. The combined organic phases are dried over sodium sulphate and concentrated to dryness. Chromatography on silica gel (dichloromethane/tetrahydrofuran: 98/2) allows 9.9 g of expected product to be obtained.

Step 2: 6-Chloro-N-{[1-(methylaminocyclopropyl)methyl}pyridin-3-amine dihydrochloride The compound is obtained according to the procedure of Step 2 of Example 1 using the compound of the above Step 1.

Mass spectrometry (ESI): m/z=212.1 Th ([M+H]⁺)
Melting point: 196-202° C.

EXAMPLE 10

6-Chloro-N-methyl-N-{[1-(methylamino)cyclopropyl)methylpyridin-3-amine dihydrochloride Step 1: tert-Butyl (1-{[(6-chloropyridin-3-yl)(formyl)amino]methyl}cyclopropyl)-methylcarbamate The compound is obtained according to the procedure of Step 1 of Example 2 using the compound of Step 1 of Example 9.

Step 2: tert-Butyl (1-{[(6-chloropyridin-3-yl)(methyl)amino]methyl}cyclopropyl)-methylcarbamate At 0° C., 2.2 ml of 10M borane-methyl sulphide complex are poured into a mixture containing 3.0 g of the product obtained in the above Step 1 and 30 ml of tetrahydrofuran. Cooling is ceased and, when the temperature has stabilised, refluxing is carried out for 3 hours. After cooling, hydrochloric methanol is poured in until pH 2 is reached. Stirring is carried out for 1 hour at 20° C. followed by refluxing for 1 hour. Concentration to dryness is carried out and the residue is taken up in a mixture of dichloromethane and 4N sodium hydroxide solution. Separation is carried out and the aqueous phase is extracted with dichloromethane. The combined organic phases are dried over sodium sulphate and concentrated to dryness. The residue is chromatographed on 200 g of silica gel (dichloromethane/tetrahydrofuran: 95/5). 1.6 g of expected product is obtained.

Step 3: 6-Chloro-N-methyl-N-{[1-methylamino) cyclopropyl]methylpyridin-3-amine dihydrochloride The product is obtained according to the procedure of Step 2 of Example 1 using the product obtained in the above Step 2.
Mass spectrometry (ESI): m/z=226.1 Th ([M+H]$^+$)
Melting point: 133-136° C.

EXAMPLE 11

6-Bromo-N-{[1-(methylaminocyclopropyl) methyl}pyridin-3-amine fumarate

Step 1: tert-Butyl (1-{[(6-bromopyridin-3-yl)amino] methyl}cyclopropyl)-methylcarbamate The product is obtained according to the procedure of Step 1 of Example 9 using 5-amino-2-bromopyridine instead of 5-amino-2-chloropyridine.

Step 2: 6-Bromo-N-{[1-(methylamino)cyclopropyl] methyl}pyridin-3-amine fumarate 3.5 ml of trifluoroacetic acid are added to a mixture containing 2 g of the product obtained in the above Step 1 and 20 ml of dichloromethane. Stirring is carried out for 20 hours at 20° C. 10% aqueous sodium carbonate solution is added until a pH of >9 is reached. Dichloromethane is added. Separation is carried out and the organic phase is dried over sodium sulphate and concentrated to dryness. The residue is taken up in 5 ml of ethanol. 0.6 g of fumaric acid dissolved in 10 ml of ethanol is added. Crystallisation is observed. The crystals are suction-filtered off, washed with ethanol and then with ether and dried at 50° C. under 1 torr. 1.6 g of expected product is obtained.
Mass spectrometry (ESI): m/z=256.0 Th ([M+H]$^+$)
Melting point: 165-169° C.

EXAMPLE 12

6-Bromo-N-methyl-N-{[1-(methylamino)cyclopropyl)methyl}pyridin-3-amine fumarate

Step 1: tert-Butyl (1-{[(6-bromopyridin-3-yl) (formyl)amino]methyl}cyclopropyl)-methylcarbamate The product is obtained according to the procedure of Step 1 of Example 2 using the compound of Step 1 of Example 11.

Step 2: tert-Butyl (1-{[(6-bromopyridin-3-yl)(methyl)amino]methyl}cyclopropyl)-methylcarbamate The product is obtained according to the procedure of Step 2 of Example 10 using the product of the above Step 1.

Step 3: 6-Bromo-N-methyl-N-{[1-(methylamino) cyclopropyl]methyl}pyridin-3-amine fumarate The product is obtained according to the procedure of Step 2 of Example 11 using the product obtained in the above Step 2.
Mass spectrometry (ESI): m/z=270.1 Th ([M+H]$^+$)
Melting point: 146-150° C.

EXAMPLE 13

6-Methyl-N-{[1-(methylamino)cyclopropyl] methyl}pyridin-3-amine dihydrochloride

Step 1: tert-Butyl methyl(1-{[(6-methylpyridin-3-yl) amino]methyl}cyclopropyl)-carbamate The compound is obtained according to the procedure of Step 1 of Example 9 using 5-amino-2-methylpyridine instead of 5-amino-2-chloropyridine.

Step 2: 6-Methyl-N-{[1-(methylamino)cyclopropyl] methyl}pyridin-3-amine dihydrochloride The compound is obtained according to the procedure of Step 2 of Example 9 using the product of the above Step 1.
Mass spectrometry (ESI): m/z=192.2 Th ([M+H]$^+$)
Melting point: 230-232° C.

EXAMPLE 14

N,6-Dimethyl-N-{[1-(methylamino)cyclopropyl] methyl}pyridin-3-amine dihydrochloride Step 1: tert-Butyl (1-{[formyl(6-methylpyridin-3-ylamino]methyl}cyclopropyl)-methylcarbamate The compound is obtained according to the procedure of Step 1 of Example 2 using the compound of Step 1 of Example 13.

Step 2: tert-Butyl methyl(1-{[methyl(6-methylpyridin-3-yl)amino]methyl}cyclopropyl)-carbamate The compound is obtained according to the procedure of Step 2 of Example 2 using the product of the above Step 1.

Step 3: N,6-Dimethyl-N-{[1-(methylamino)cyclopropyl]methyl}pyridin-3-amine dihydrochloride The compound is obtained according to the procedure of Step 2 of Example 1 using the product obtained in the above Step 2.
Mass spectrometry (ESI): m/z=206.2 Th ([M+H]$^+$)
Melting point: 112-115° C.

EXAMPLE 15

6-Chloro-N-{[1-(dimethylamino)cyclopropyl] methyl}pyridin-3-amine dihydrochloride The compound is obtained according to the procedure of Example 5 with replacement of the compound of Example 4 with the compound of Example 9.
Mass spectrometry (EI): m/z 225.1 Th (M$^+$)
Melting point: 158-160° C.

EXAMPLE 16

6-Chloro-N-{[1-(dimethylamino)cyclopropyl]methyl}-N-methylpyridin-3-amine dihydrochloride

Step 1: (6-Chloropyridin-3-yl)({1-[formyl(methyl)amino]cyclopropyl}methyl)formamide Over a period of 15 minutes, 1.85 ml of formic acid are added to 3.7 ml of acetic anhydride at 5° C., and then the mixture is heated for 2 hours at 55° C. After returning to ambient temperature, 7.4 ml of tetrahydrofuran are added and then the reaction mixture is cooled to –20° C. Over a period of 30 minutes, a solution of 1.57 g of the base of the compound of Example 9 in 18.5 ml of tetrahydrofuran is poured in. The temperature is maintained at –20° C. for one hour and then at 0° C. for 20 hours. Concentration is carried out, and the residue is taken up in 10% aqueous sodium carbonate solution and extracted with dichloromethane. The dichloromethane is dried over sodium sulphate and concentration to dryness is carried out. Chromatography on silica gel (dichloromethane/methanol: 97.5/2.5) allows 1.73 g of the expected product to be obtained.

Step 2: 6-Chloro-N-{[1-(dimethylamino)cyclopropyl]methyl}-N-methylpyridin-3-amine dihydrochloride 1.73 g of the compound obtained in the above Step 1 are dissolved in 48 ml of tetrahydrofuran and then 3.6 ml of 10M borane-methyl sulphide complex are added. Stirring is carried out for 20 hours at 20° C. followed by refluxing for 3 hours. Cooling to 5° C. is carried out and 6.5 ml of methanol are poured in; stirring is carried out for one hour and concentration to dryness is carried out. The residue is taken up in dichloromethane and washed with 10% aqueous sodium hydrogen carbonate solution. The organic phase is dried over sodium sulphate and concentrated and chromatography of the residue on silica gel (dichloromethane/methanol: 97.5/2.5) allows the base of the expected product to be obtained. 0.7 g of that base are dissolved in 5 ml of isopropanol and a solution of hydrochloric acid in ether is added to obtain, after filtering off a precipitate and drying, 0.85 g of the expected compound.
Mass spectrometry (ESI): m/z 240.1 Th ([M+H]$^+$)
Melting point: 163-166° C.

EXAMPLE 17

N-Benzyl-6-chloro-N-{[1-(methylamino)cyclopropyl]methyl}pyridin-3-amine dihydrochloride

Step 1: tert-Butyl (1-{[benzoyl(6-chloropyridin-3-yl)amino]methyl}cyclopropyl)-methylcarbamate 10.17 g of the compound obtained in Step 1 of Example 9 are dissolved in 200 ml of tetrahydrofuran, 4.88 ml of triethylamine are added, cooling to 5° C. is carried out and, over a period of 30 minutes, 5.05 g of benzoyl chloride are poured in. Stirring is carried out for one hour at 5° C. and then for one hour at ambient temperature, and subsequently refluxing is carried out for 2 hours. Concentration to dryness is carried out and the residue is taken up in dichloromethane and washed with 50% aqueous potassium carbonate solution. The organic phase is dried over sodium sulphate and concentrated, and chromatography of the residue on silica gel (dichloromethane/tetrahydrofuran: 96/4) allows 13.9 g of expected product to be obtained.

Step 2: tert-Butyl (1-{[benzyl(6-chloropyridin-3-yl)amino]methyl}cyclopropyl)-methylcarbamate 13.8 g of the compound obtained in the above Step 1 are dissolved in 120 ml of tetrahydrofuran, cooling to 5° C. is carried out and then 8.3 ml of 10M borane-methyl sulphide complex are added. After returning to ambient temperature, refluxing is carried out for 3 hours. Cooling to 5° C. is carried out and 15.1 ml of methanol are poured in; stirring is carried out for one hour followed by acidification to pH 3 using a solution of hydrochloric acid in methanol. Refluxing is carried out for one hour, followed by concentration to dryness. The residue is taken up in dichloromethane and washed with 10% aqueous sodium carbonate solution. The organic phase is dried over sodium sulphate and concentrated, and chromatography of the residue on silica gel (dichloromethane to dichloromethane/butanone: 90/10) allows 6.7 g of the expected compound to be obtained.

Step 3: N-Benzyl-6-chloro-N-{[1-(methylamino)cyclopropyl]methyl}pyridin-3-amine dihydrochloride The compound is obtained according to the procedure of Step 2 of Example 1, with replacement of the compound of Step 1 of Example 1 with the compound of the above Step 2.
Mass spectrometry (ESI): m/z 302.1 Th ([M+H]$^+$)
Melting point: 156-157° C.

EXAMPLE 18

N-Benzyl-6-chloro-N-{[1-(dimethylamino)cyclopropyl]methyl}pyridin-3-amine hydrochloride 3.1 g of the base of the compound of Example 17 are dissolved in 60 ml of formic acid. 60 ml of 37% aqueous formaldehyde solution are added and the mixture is heated for 4 hours at 70° C. Concentration to dryness is carried out, and the residue is taken up in 50% aqueous potassium carbonate solution and extraction is carried out with dichloromethane. The organic phase is dried over sodium sulphate, concentration is carried out, and the residue is chromatographed on silica gel (dichloromethane/acetone: 96/4). A fraction consisting of 0.48 g of base of the expected compound is isolated which, after dissolution in 5 ml of ethanol and addition of hydrochloric acid solution in ether, allows, after filtering off a precipitate and drying, 0.4 g of the expected compound to be obtained.
Mass spectrometry (ESI): m/z 316.16 Th ([M+H]$^+$)
Melting point: 190-192° C.

EXAMPLE A

Displacement of Binding of [$^{125}$I]-α-bungarotoxin on Nicotinic Receptors of the Electric Organ of Torpedo Fish This study, carried out according to the method described in J. Pharmacol. Exp. Ther., 1994, 271; 624-631, is aimed at assessing the affinity of compounds of the present invention for nicotinic receptors of the "muscular" type.

Membranes (1-5 μg/ml) of the electric organ of torpedo fish are incubated (1 hour, 22° C.) in the presence of a series of concentrations (0.01-10 μM) of each compound of the invention (diluted starting from a 10 mM stock solution in DMSO) in the presence of [$^{125}$I]-α-bungarotoxin (S.A.: 7.4 TBq/mmol: 0.2 nM) in Krebs buffer (Tris-HCl 50 mM, KCl 5 mM, MgCl$_2$ 1 mM, CaCl$_2$ 2 mM, NaCl 100 mM, pH 7.4) with 0.01% BSA; final volume: 500 μl. The non-specific binding is determined by incubating membranes in the presence of α-bungarotoxin (1 μM).

The results show that, up to a concentration of 10 μM, all of the compounds of the present invention have no significant affinity for nicotinic receptors of the "muscular" type ($K_i$>10$^{-5}$M).

EXAMPLE B

Displacement of Binding of [$^3$H]-epibatidine on Nicotinic Receptors of IMR32 Cells This study, carried out according to the technique described in Molec. Pharmacol., 1995, 48; 280-287, is aimed at determining the affinity of compounds of the present invention for nicotinic receptors of the "ganglionic" type (American Soc. Neuroscience, 2000, 26, 138).

Membranes (250 μg/ml) of IMR-32 neuroblastoma cells are incubated (2 hours, 20° C.) in the presence of a series of concentrations (0.01-10 μM) of each compound of the invention (diluted starting from a 10 mM stock solution in DMSO) and (±)-[$^3$H]-epibatidine (S.A.: 2464 GBq/mmol: 1.5 nM) in phosphate buffer (NaH$_2$PO$_4$ 20 mM, pH 7.4); final volume: 250 μl. The non-specific binding is determined by incubating membranes in the presence of 300 μM of (−)nicotine.

The results show that, up to a concentration of 10 μM, all of the compounds of the present invention have no significant affinity for nicotinic receptors of the "ganglionic" type ($K_i$>10$^{-5}$M).

EXAMPLE C

Displacement of Binding of [$^3$H]-oxotremorine-M on Muscarinic Receptors of Rat Brain This study, carried out according to the method described in Naumyn-Schmiederberg's Arch. Pharmacol., 2001, 363, 429-438, is aimed at determining the affinity of compounds of the present invention for muscarinic receptors.

Membranes (250 μg/ml) of rat brain are incubated (2 hours, 20° C.) in the presence of a series of concentrations (0.01-10 μM) of each compound of the invention (diluted starting from a 10 mM stock solution in DMSO) and [$^3$H]-oxotremorine-M (S.A.: 3174 GBq/mmol: 2 nM) in phosphate buffer (NaH$_2$PO$_4$ 20 mM, pH 7.4); final volume: 250 μl. The specific binding is determined by incubating membranes in the presence of atropine (1 μM). The affinity of the compounds of the present invention for muscarinic receptors is characterised by determination of the $K_i$.

The results show that, up to a concentration of 10 μM, all of the compounds of the present invention have no affinity for muscarinic receptors ($K_i$>10$^{-5}$M).

EXAMPLE D

Displacement of Binding of [$^{125}$I]-α-bungarotoxin on "Type α7" Nicotinic Receptors of Rat Brain This study, carried out according to the method described in Molec. Pharmacol., 1986, 30; 427-436, is aimed at determining the affinity of compounds of the present invention for type α7 central nicotinic receptors.

Membranes (1000 μg/ml) of rat brain are incubated (5 hours, 37° C.) in the presence of a series of concentrations (0.01-10 μM) of each compound of the present invention (diluted starting from a 10 mM stock solution in DMSO) and [$^{125}$I]-α-bungarotoxin (S.A.: 7.4 TBq/mmol: 1 nM) in Krebs buffer (Tris-HCl 50 mM, KCl 5 mM, MgCl$_2$ 1 mM, CaCl$_2$ 2 mM, NaCl 100 mM, pH 7.4) with 0.05% BSA; final volume: 500 μl. The non-specific binding is determined by incubating membranes in the presence of α-bungarotoxin (1 μM).

The affinity of compounds of the present invention for type α7 nicotinic receptors is characterised by determination of the $K_i$.

The results indicate that, up to a concentration of 10 μM, the majority of the compounds of the present invention have no affinity for type α7 central nicotinic receptors. Certain compounds of the invention have a $K_i$ of the order of 10 μM, such as Example 2, which has a $K_i$ of 8.3×10$^{-6}$M.

EXAMPLE E

Displacement of Binding of [$^3$H]-cytisine on "Type α4β2" Nicotinic Receptors of Rat Brain This study, carried out according to the technique described in Molec. Pharmacol., 1990, 39; 9-12, is aimed at determining the affinity of compounds of the present invention for type α4β2 central nicotinic receptors.

Membranes (250 μg/ml) of rat brain are incubated (2 hours, 20° C.) in the presence of a series of concentrations (0.01-10 μM) of each compound of the present invention (diluted starting from a 10 mM stock solution in DMSO) and [$^3$H]-cytisine (S.A.: 1184 GBq/mmol: 2 nM) in phosphate buffer (NaH$_2$PO$_4$ 20 mM, pH 7.4); final volume: 250 μl. The non-specific binding is determined by incubating membranes in the presence of 10 μM of (−)nicotine. The affinity of the compounds of the present invention for type α4β2 central nicotinic receptors is characterised by determination of the $K_i$.

The results obtained show that the compounds of the present invention have a strong affinity for type α4β2 central nicotinic receptors. Thus, Examples 1, 2 and 10 have $K_i$ values of 3.4×10$^{-8}$M, 1.5×10$^{-8}$M and 1.6×10$^{-8}$M, respectively.

These results, and also those obtained in Examples A to D, indicate that the compounds of the present invention are powerful central nicotinic ligands that are specific to type α4β2 receptors.

EXAMPLE F

In vivo Measurement of the Release of Acetylcholine by Means of Intra-Cortical Microdialysis in the Conscious Wistar Rat The systemic administration of nicotine and nicotinic agonists causes an increase, in vivo, of acetylcholine in various regions of the brain (Neurochem. Res., 1996, 21, 1181-1186; Eur. J. Pharmacol., 1998, 351, 181-188; Br. J. Pharmacol., 1999, 127, 1486-1494). A microdialysis probe is implanted in the median prefrontal cortex of male Wistar rats. Six or seven days after they have been implanted, the probes are perfused with Ringer's solution (NaCl 147 mM, KCl 2.7 mM, CaCl$_2$ 1.2 mM, MgCl$_2$ 1 mM, neostigmine 20 nM) at a flow rate of 1 μl/min, the animal being free to move. After 2 hours in the animal quarters, the product under test is administered by the intraperitoneal route. A group of control animals receives the solvent used for the product. The dialysates (30 μl) are then collected every 30 minutes for 4 hours in order to measure the cortical extra-synaptic concentrations of acetylcholine by means of HPLC with amperometric detection. The results are expressed in pg of acetylcholine/dialysate, and inter-group comparisons are carried out by means of variance analysis using 2 factors (treatment×time), with measurements being repeated over time.

The results obtained show that the compounds of the present invention increase, in vivo, the cortical release of acetylcholine in a dose-dependent manner for doses ranging from 0.3 to 3 mg/kg IP, indicating the α4β2-agonist character. Thus, Examples 1 and 2, one hour after administration at a dose of 3 mg/km IP, induces an increase of +70% and +80%, respectively, in the release of acetylcholine in the prefrontal cortex of the conscious Wistar rat.

EXAMPLE G

Abdominal Contractions Induced by phenyl-p-benzoquinone (PBQ) in the NMRI Mouse

Intraperitoneal administration of an alcoholic solution of PBQ causes abdominal cramps in the mouse (Proc. Soc. Exp. Biol., 1957, 95, 729-731). The cramps are characterised by repeated contractions of the abdominal musculature, accompanied by extension of the hind limbs. Most analgesics antagonise these abdominal cramps (Brit. J. Pharmacol. Chem., 1968, 32, 295-310). At t=0 min., the animals are weighed and the compound being studied is administered by the IP route. A group of control animals is given the solvent used for the compound. At t=30 min., an alcoholic solution of PBQ (0.2%) is administered by the IP route in a volume of 0.25 ml/mouse. Immediately after administration of the PBQ, the animals are placed in cylinders of plexiglass (L=19.5 cm; I.D.=5 cm). From t=35 min. to t=45 min., the animals' reaction is observed and the experimenter notes the total number of abdominal cramps per animal. The results are expressed as the percentage inhibition of the number of abdominal cramps measured in the control animals, at the active dose of the compound studied.

The results obtained show inhibition of the order of −80% for active doses of 10 mg/kg IP, which demonstrates that the compounds of the invention possess antalgic properties. Thus, Examples 1, 2, 9 and 10, administered at a dose of 10 mg/kg IP, reduce by −50%, −76%, −52% and −69%, respectively, the number of abdominal cramps caused by the administration of PBQ to the mouse.

EXAMPLE H

Social Recognition in the Wistar Rat

Initially described in 1982 (J. Comp. Physiol., 1982, 96, 1000-1006), the social recognition test has subsequently been proposed by various authors (Psychopharmacology, 1987, 91, 363-368 ; Psychopharmacology, 1989, 97, 262-268) for studying the mnemocognitive effects of new compounds. The test is based on the natural expression of the olfactory memory of the rat and its natural tendency to forget and allows evaluation of memorisation, by recognition of a young congeneric animal, by an adult rat. A young rat (21 days), taken at random, is placed for 5 minutes in the cage housing an adult rat. With the aid of a video device, the experimenter observes the social recognition behaviour of the adult rat and measures its overall duration. The young rat is then removed from the adult rat's cage and is placed in its own cage until the second introduction. The adult rat is given the compound under test by the intraperitoneal route and, after 2 hours, is again brought into the presence (5 minutes) of the young rat. The social recognition behaviour is then observed again and its duration measured. The assessment criterion is the difference (T2−T1), expressed in seconds, between the "recognition" times of the 2 encounters.

The results obtained show a difference (T2−T1) ranging from −19 s to −36 s for doses ranging from 1 to 3 mg/kg IP, which shows that the compounds of the invention very greatly enhance memorisation, even at a low dose. Thus, Examples 1, 2 and 4, at a dose of 3 mg/kg IP, induce a difference (T2−T1) of 36, 29 and 19 s, respectively.

EXAMPLE I

Object Recognition in the Wistar Rat

The object recognition test in the Wistar rat (Behav. Brain Res., 1988, 31, 47-59) is based on the spontaneous exploratory activity of the animal and has the characteristics of episodic memory in humans. Sensitive to ageing (Eur. J. Pharmacol., 1997, 325, 173-180), as well as to cholinergic dysfunctions (Pharm. Biochem. Behav., 1996, 5(2), 277-283), this memory test is based on the differential exploration of 2 objects of fairly similar size, one familiar and the other new. Before the test, the animals are accustomed to the environment (enclosure without object). During a 1st session, the rats are placed (for 3 minutes) in an enclosure containing 2 identical objects. The duration of exploration of each object is measured. During the second session (3 minutes), 24 hours later, 1 of the 2 objects is replaced by a new object. The duration of exploration of each object is measured. The assessment criterion is the difference Delta, expressed in seconds, between the exploration times of the new object and the familiar object during the $2^{nd}$ session. The control animals, treated beforehand with carrier by the oral route 60 minutes before each session, explore the familiar object and the new object in an identical way, indicating that the object already presented has been forgotten. The animals treated with mnemocognitive facilitator compound preferentially explore the new object, indicating that the object already presented has been remembered.

The results obtained show a difference Delta of the order of 9 s for doses ranging from 0.01 to 0.3 mg/kg PO, demonstrating that the compounds of the invention greatly enhance memorisation, even at a very low dose. Thus, administered at a dose of 0.3 mg/kg PO, Examples 1 and 2 cause a difference Delta of 9 and 4 s, respectively.

EXAMPLE J

Pharmaceutical Compositions for 1000 Tablets each Containing 10 mg of Active Ingredient

| | |
|---|---|
| Compound of Example 1 | 10 g |
| Hydroxypropyl methyl cellulose | 10 g |
| Wheat starch | 15 g |
| Lactose | 90 g |
| Magnesium stearate | 2 g |

The invention claimed is:

1. A compound selected from those of formula (I):

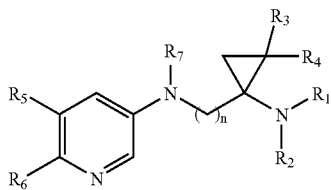

wherein:
- n represents an integer from 1 to 6 inclusive,
- $R_1$ and $R_2$, which may be identical or different, each independently of the other represent a hydrogen atom, a linear or branched $(C_1\text{-}C_6)$alkyl group or an aryl-$(C_1\text{-}C_6)$alkyl group in which the alkyl moiety may be linear or branched,
- $R_3$ and $R_4$, which may be identical or different, each independently of the other represent a hydrogen atom or a linear or branched $(C_1\text{-}C_6)$alkyl group,
- $R_5$ and $R_6$, which may be identical or different, each independently of the other represent a hydrogen atom or a linear or branched $(C_1\text{-}C_6)$alkyl, halogen, hydroxy, linear or branched $(C_1\text{-}C_6)$alkoxy, cyano, nitro, linear or branched $(C_2\text{-}C_6)$acyl, linear or branched $(C_1\text{-}C_6)$alkoxycarbonyl, linear or branched $(C_1\text{-}C_6)$trihaloalkyl or linear or branched $(C_1\text{-}C_6)$trihaloalkoxy group or an amino group optionally substituted by one or two linear or branched $(C_1\text{-}C_6)$alkyl groups,
- $R_7$ represents a hydrogen atom, a linear or branched $(C_1\text{-}C_6)$alkyl group or an aryl-$(C_1\text{-}C_6)$alkyl group in which the alkyl moiety may be linear or branched,
- it being understood that an aryl group means phenyl, biphenyl, naphthyl, dihydronaphthyl, tetrahydronaphthyl, indanyl or indenyl group, each of the groups being optionally substituted by one or more identical or different groups selected from halogen, linear or branched $(C_1\text{-}C_6)$alkyl, hydroxy, cyano, nitro, linear or branched $(C_1\text{-}C_6)$alkoxy, linear or branched $(C_2\text{-}C_7)$acyl, linear or branched $(C_1\text{-}C_6)$alkoxycarbonyl, linear or branched $(C_1\text{-}C_6)$trihaloalkyl and linear or branched $(C_1\text{-}C_6)$trihaloalkoxy groups and amino groups optionally substituted by one or two linear or branched $(C_1\text{-}C_6)$alkyl groups,
- its enatiomers, diastereoisomers and additional salts thereof with a pharmaceutically acceptable acid or base.

2. The compound of claim 1, wherein n is an integer having the value 1, its enantiomers, diastereoisomers, and addition salts thereof with a pharmaceutically acceptable acid or base.

3. The compound of claim 1, wherein $R_1$ and $R_2$, which may be identical or different, each independently of the other represent a hydrogen atom or a linear or branched $(C_1\text{-}C_6)$alkyl group, its enantiomers, diastereoisomers, and addition salts thereof with a pharmaceutically acceptable acid or base.

4. The compound of claim 1, wherein $R_3$ and $R_4$ represent a hydrogen atom, its enantiomers, diastereoisomers, and addition salts thereof with a pharmaceutically acceptable acid or base.

5. The compound of claim 1, wherein $R_5$ and $R_6$, which may be identical or different, each independently of the other represent a hydrogen atom or a linear or branched $(C_1\text{-}C_6)$alkyl group, its enantiomers, diastereoisomers, and addition salts thereof with a pharmaceutically acceptable acid or base.

6. The compound of claim 1, wherein $R_7$ represents a hydrogen atom or a linear or branched $(C_1\text{-}C_6)$alkyl group, its enantiomers, diastereoisomers, and addition salts thereof with a pharmaceutically acceptable acid or base.

7. The compound of claim 1 which is selected from:
- N-{[1-(methylamino)cyclopropyl]methyl}pyridin-3-amine,
- N-methyl-N-{[1-(methylamino)cyclopropyl]methyl}pyridin-3-amine,
- N-[(1-aminocyclopropyl)methyl]pyridin-3-amine,
- N-{[1-(dimethylamino)cyclopropyl]methyl}pyridin-3-amine,
- N-[(1-aminocyclopropyl)methyl]-N-methylpyridin-3-amine,
- N-{[1-(dimethylamino)cyclopropyl]methyl}-N-methylpyridin-3-amine,
- 6-chloro-N-{[1-(methylamino)cyclopropyl]methyl}pyridin-3-amine,
- 6-chloro-N-methyl-N-{[1-(methylamino)cyclopropyl]methyl}pyridin-3-amine,
- 6-bromo-N-{[1-(methylamino)cyclopropyl]methyl}pyridin-3-amine,
- 6-bromo-N-methyl-N-{[1-(methylamino)cyclopropyl]methyl}pyridin-3-amine,
- 6-methyl-N-{[1-(methylamino)cyclopropyl]methyl}pyridin-3-amine, and
- N,6-dimethyl-N-{[1-(methylamino)cyclopropyl]methyl}pyridin-3-amine, its enantiomers, diastereoisomers, and addition salts thereof with a pharmaceutically acceptable acid or base.

8. A pharmaceutical composition comprising as active ingredient a compound according to claim 1, alone or in combination with one or more pharmaceutically acceptable, inert, non-toxic excipients or carriers.

* * * * *